United States Patent [19]
Viola et al.

[11] Patent Number: 5,807,376
[45] Date of Patent: Sep. 15, 1998

[54] APPARATUS AND METHOD FOR PERFORMING SURGICAL TASKS DURING LAPAROSCOPIC PROCEDURES

[75] Inventors: Frank J. Viola, Sandy Hook; Dominick L. Mastri, Bridgeport; Ghaleb A. Sater, Shelton, all of Conn.; Wayne P. Young, Brewster, N.Y.; Frank M. Rende, III, Stamford, Conn.

[73] Assignee: United States Surgical Corporation, Norwalk, Conn.

[21] Appl. No.: 428,046

[22] Filed: Apr. 25, 1995

Related U.S. Application Data

[62] Division of Ser. No. 265,353, Jun. 24, 1994, abandoned.

[51] Int. Cl.$^6$ .................................................. B25J 1/00
[52] U.S. Cl. .......................... 606/1; 901/30; 901/39; 623/64; 414/2; 414/1
[58] Field of Search .............................. 606/1; 294/19.1, 294/24, 25; 414/1, 2, 3, 7; 623/64, 65; 901/30, 31, 33, 36, 39

[56] References Cited

U.S. PATENT DOCUMENTS

| | | |
|---|---|---|
| 1,225,415 | 5/1917 | Cronemiller . |
| 1,507,682 | 9/1924 | Pecorella et al. . |
| 2,553,827 | 5/1951 | Mason . |
| 3,188,753 | 6/1965 | Lovercheck . |
| 3,694,021 | 9/1972 | Mullen . |
| 3,866,966 | 2/1975 | Skinner, II . |
| 3,901,547 | 8/1975 | Sinnner, II . |
| 4,094,016 | 6/1978 | Eroyan . |
| 4,208,830 | 6/1980 | Yoshida . |
| 4,246,661 | 1/1981 | Pinson . |
| 4,315,650 | 2/1982 | Yoshida . |
| 4,466,649 | 8/1984 | Ozawa . |
| 4,469,091 | 9/1984 | Slanetz, Jr. . |
| 4,643,473 | 2/1987 | Douglas . |
| 4,834,761 | 5/1989 | Walters ............................ 414/7 |
| 4,921,293 | 5/1990 | Ruoff et al. . |
| 4,946,380 | 8/1990 | Lee . |
| 5,062,673 | 11/1991 | Mimura . |
| 5,080,681 | 1/1992 | Erb . |
| 5,080,682 | 1/1992 | Schectman . |
| 5,086,401 | 2/1992 | Glassman et al. . |
| 5,092,646 | 3/1992 | Smallridge . |
| 5,195,505 | 3/1993 | Josefsen . |
| 5,200,679 | 4/1993 | Graham . |
| 5,441,494 | 8/1995 | Ortiz ............................... 606/1 |

FOREIGN PATENT DOCUMENTS

| | | |
|---|---|---|
| 04907114 | 11/1990 | European Pat. Off. . |
| 0640319 | 7/1994 | European Pat. Off. . |
| 2602170 | 7/1986 | France . |
| 3709706 | 10/1987 | Germany . |
| 4306786 | 3/1993 | Germany . |
| 4223792 | 9/1993 | Germany . |
| 43 06 786 | 10/1994 | Germany . |

OTHER PUBLICATIONS

Fisher, Scott S., "Telepresence Master Glove Controller for Dextrous Robotic End–effectors", SPIE vol. 726, pp. 396–401, 1986.

"Medica News in Brief: Endohand Allows Minimally Invasive Palpation", *Clinica*, 581, Dec. 8, 1993, p. 16.

"Giving Deaf/Blind People a Hand".

*Primary Examiner*—Michael Peffley

[57] ABSTRACT

An apparatus is provided for performing surgical tasks during laparoscopic procedures which includes an elongated body, a mechanical hand operatively associated with a distal portion of the elongated body and including a plurality of articulated fingers, and an actuation assembly operatively associated with the proximal portion of the elongated body for controlling the operation of the mechanical hand.

27 Claims, 17 Drawing Sheets

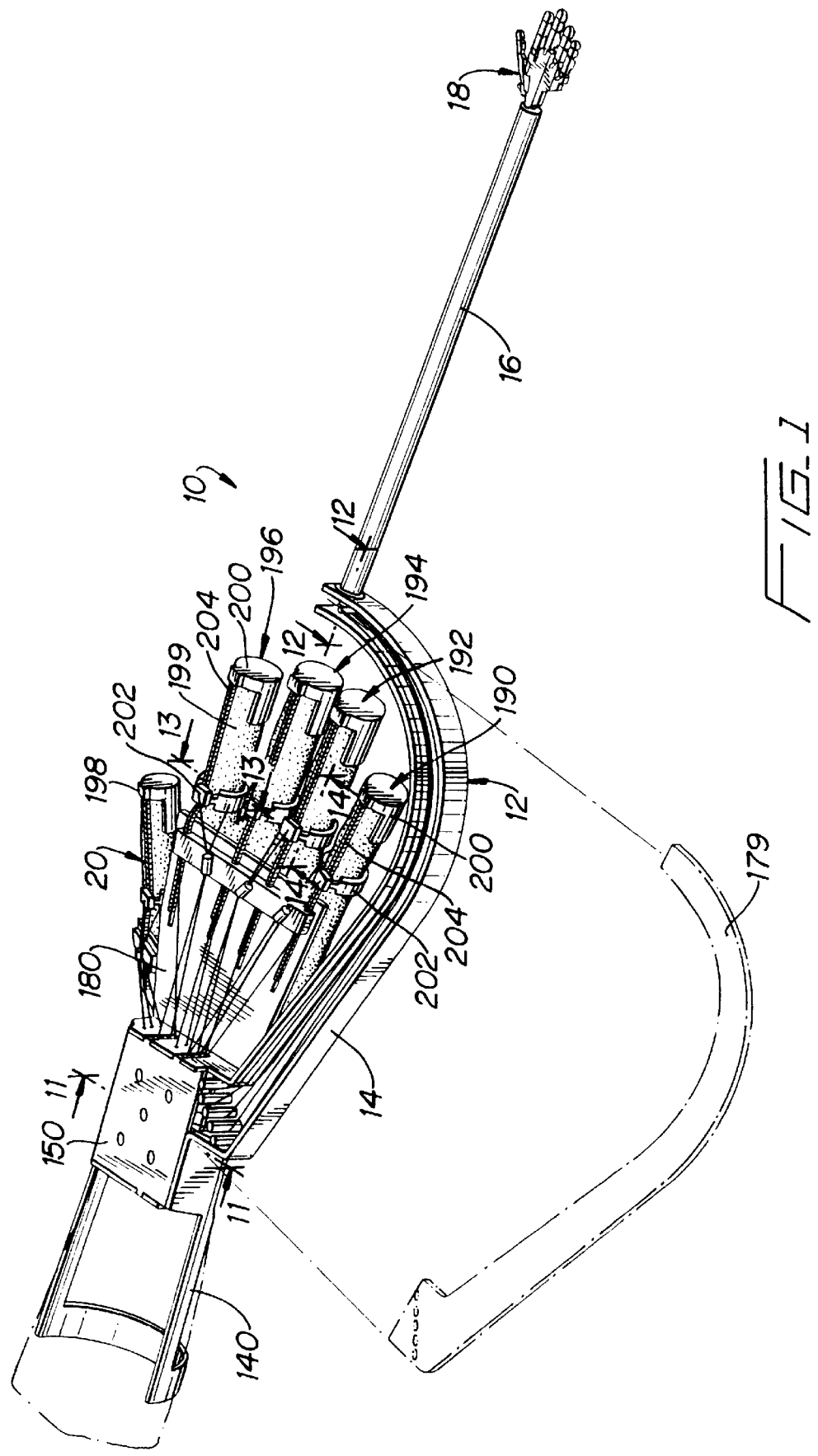

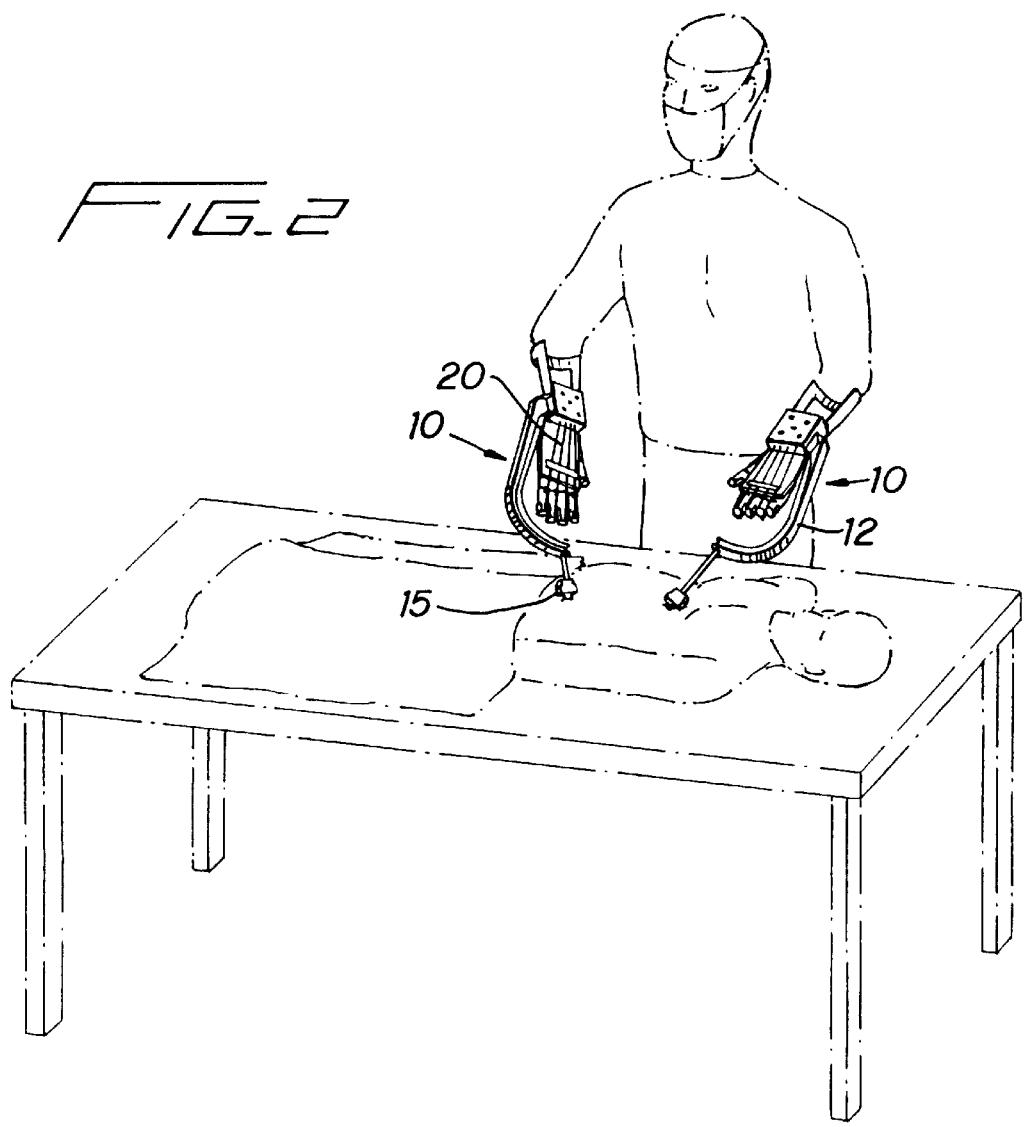
FIG_2
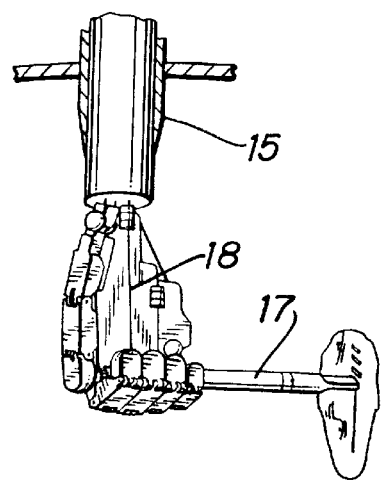
FIG_3A
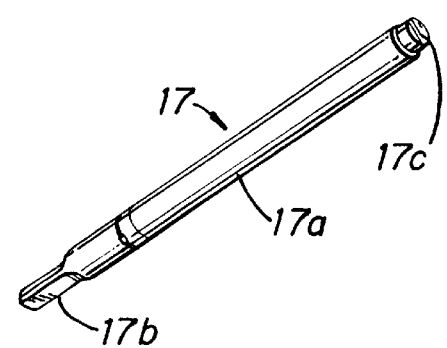
FIG_3B

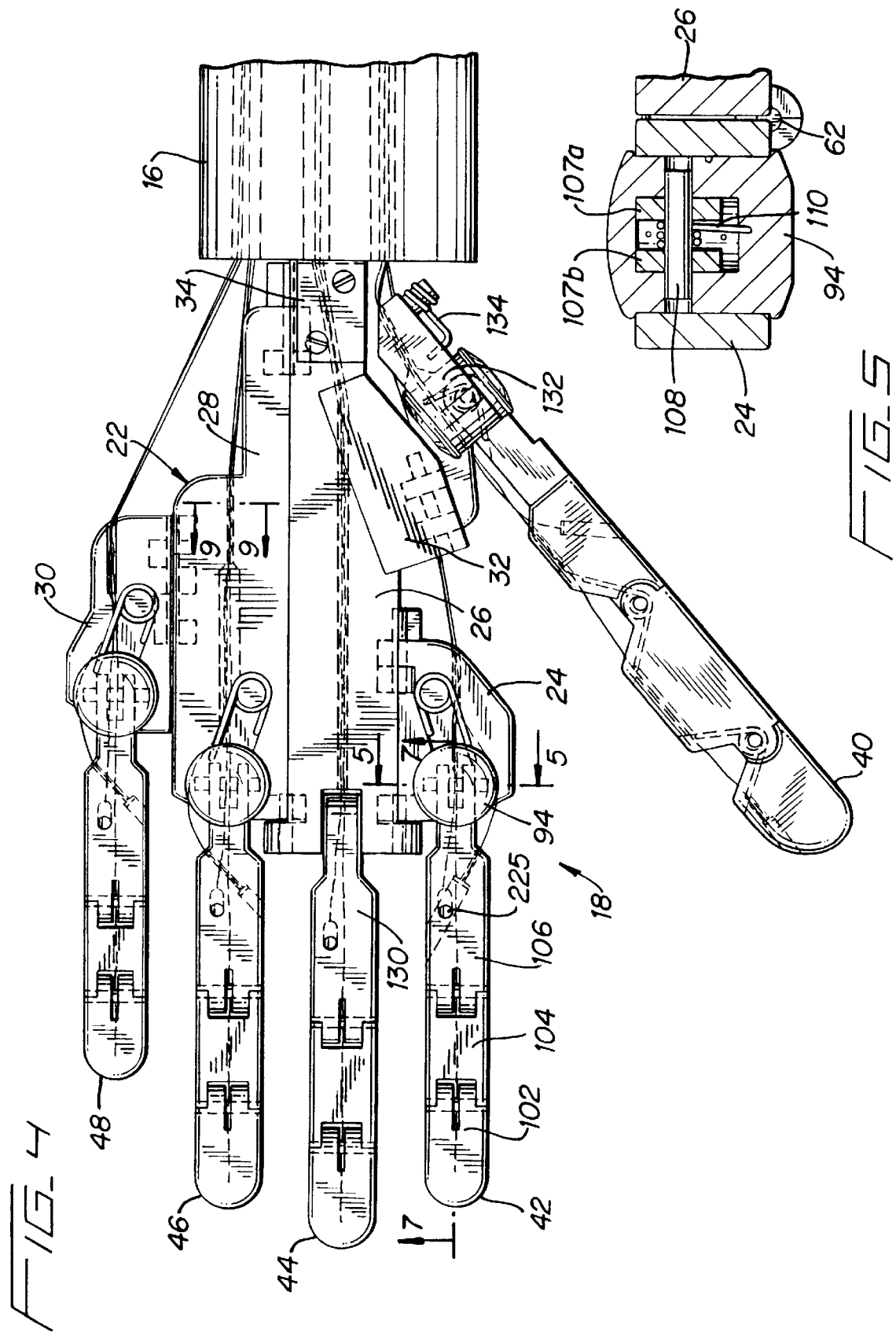

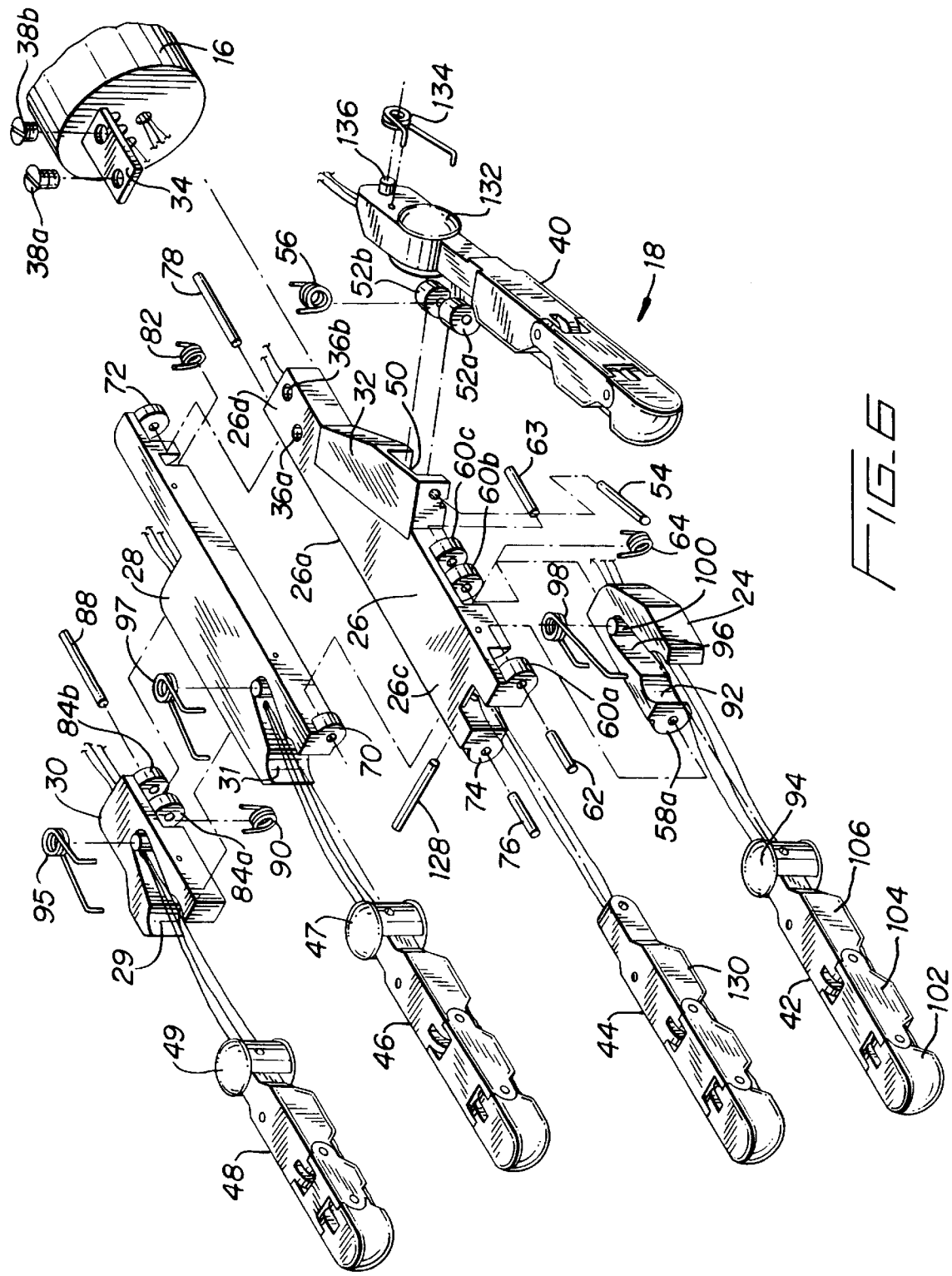

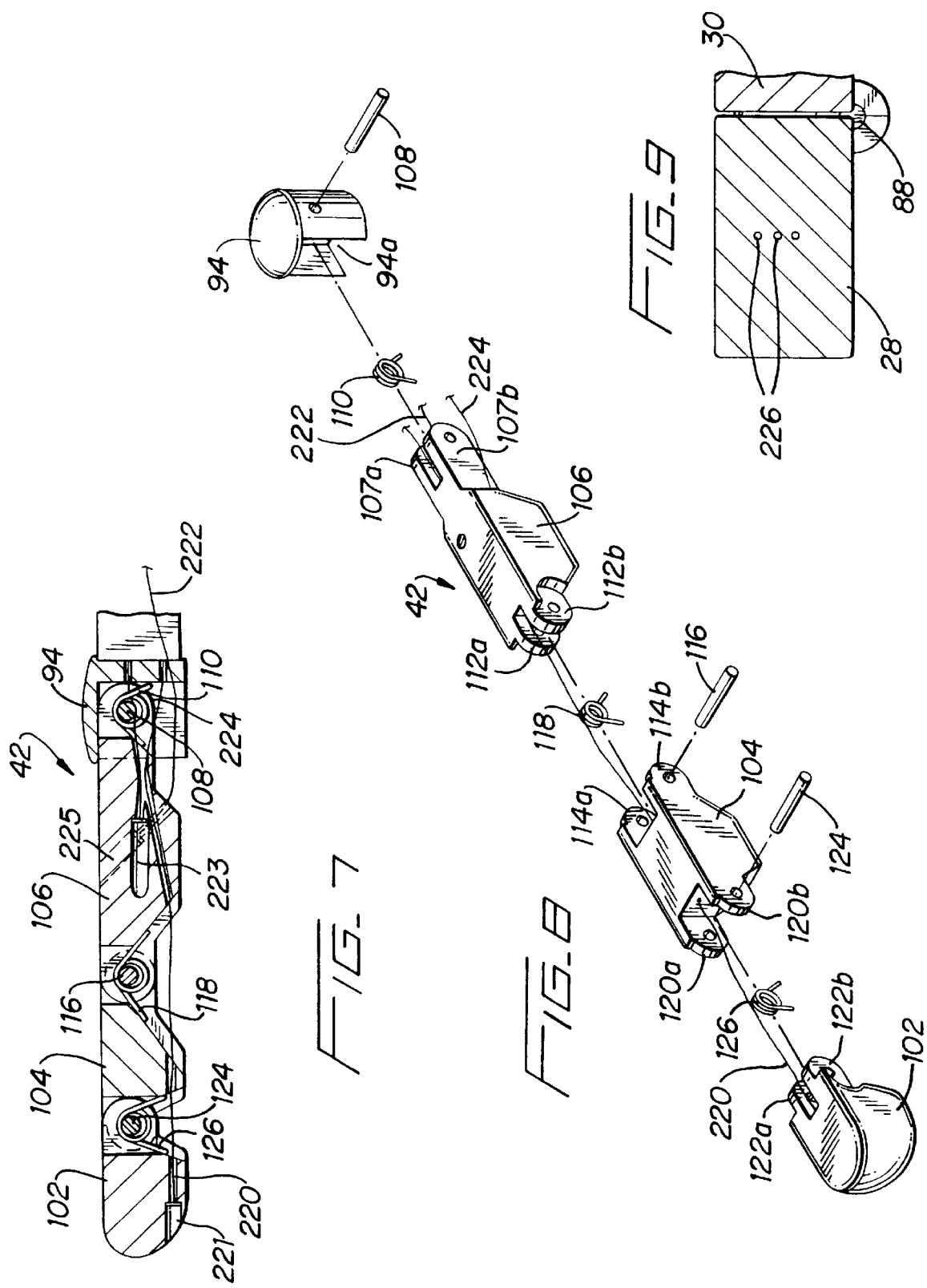

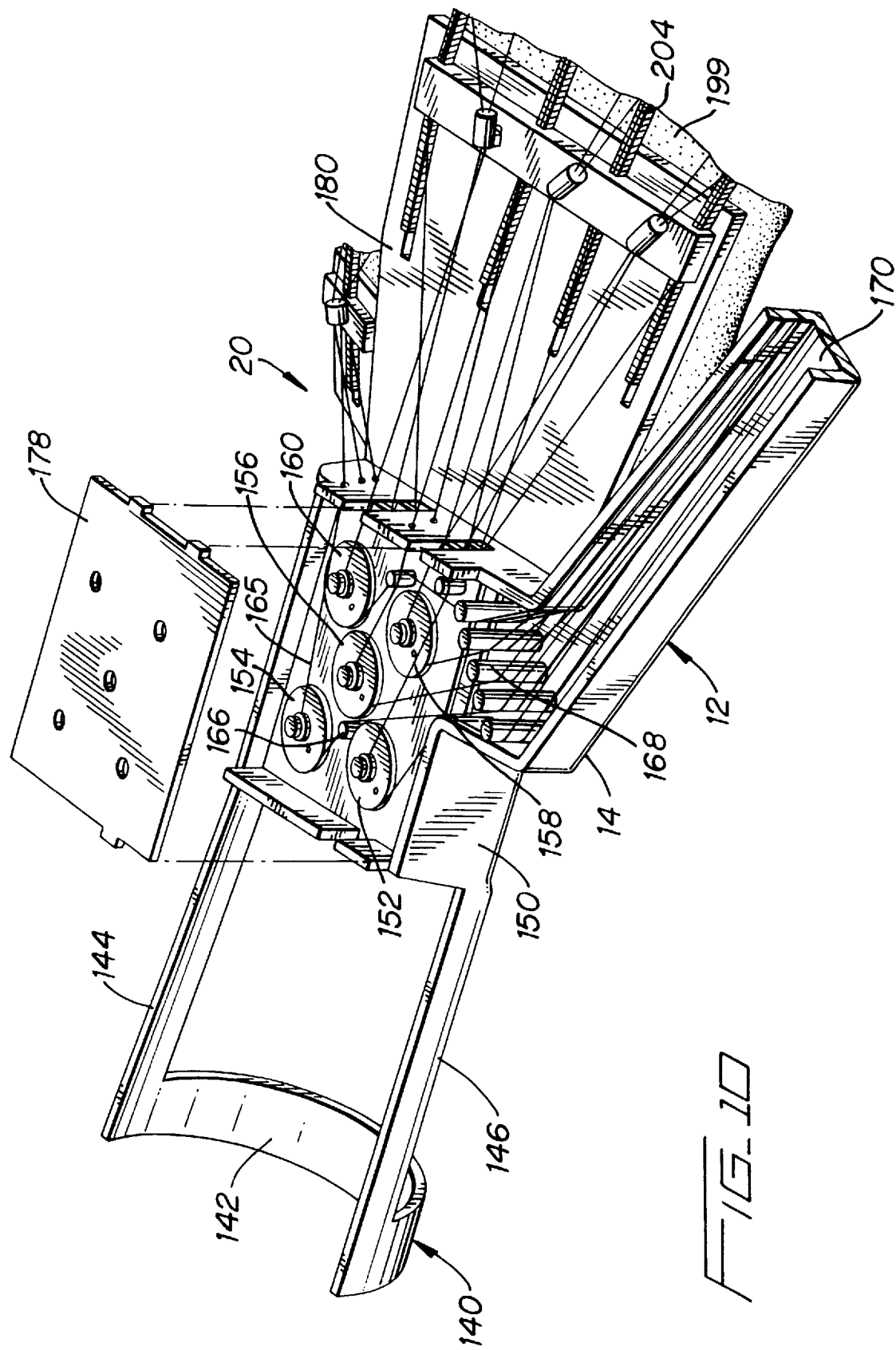

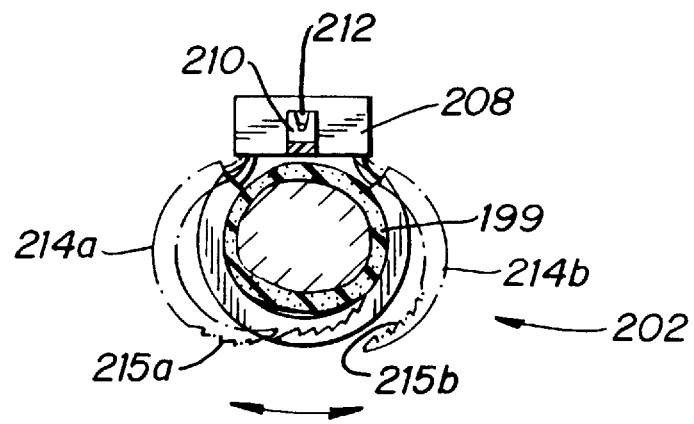
FIG_13
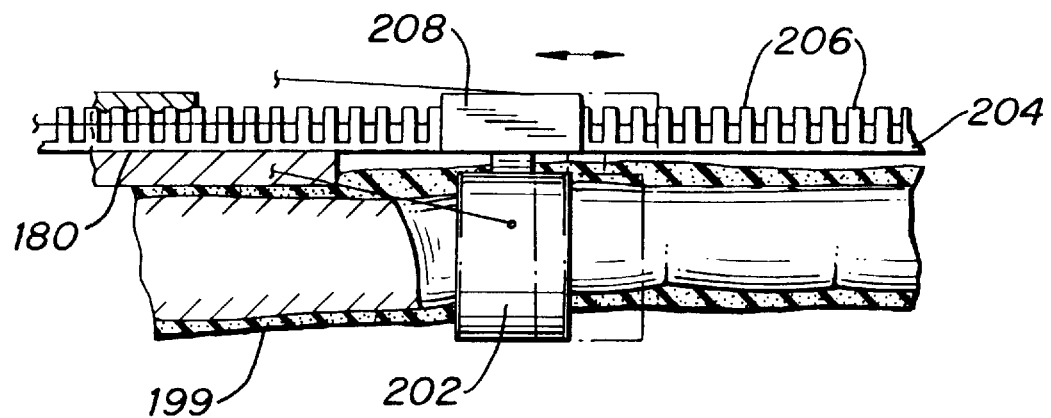
FIG_14

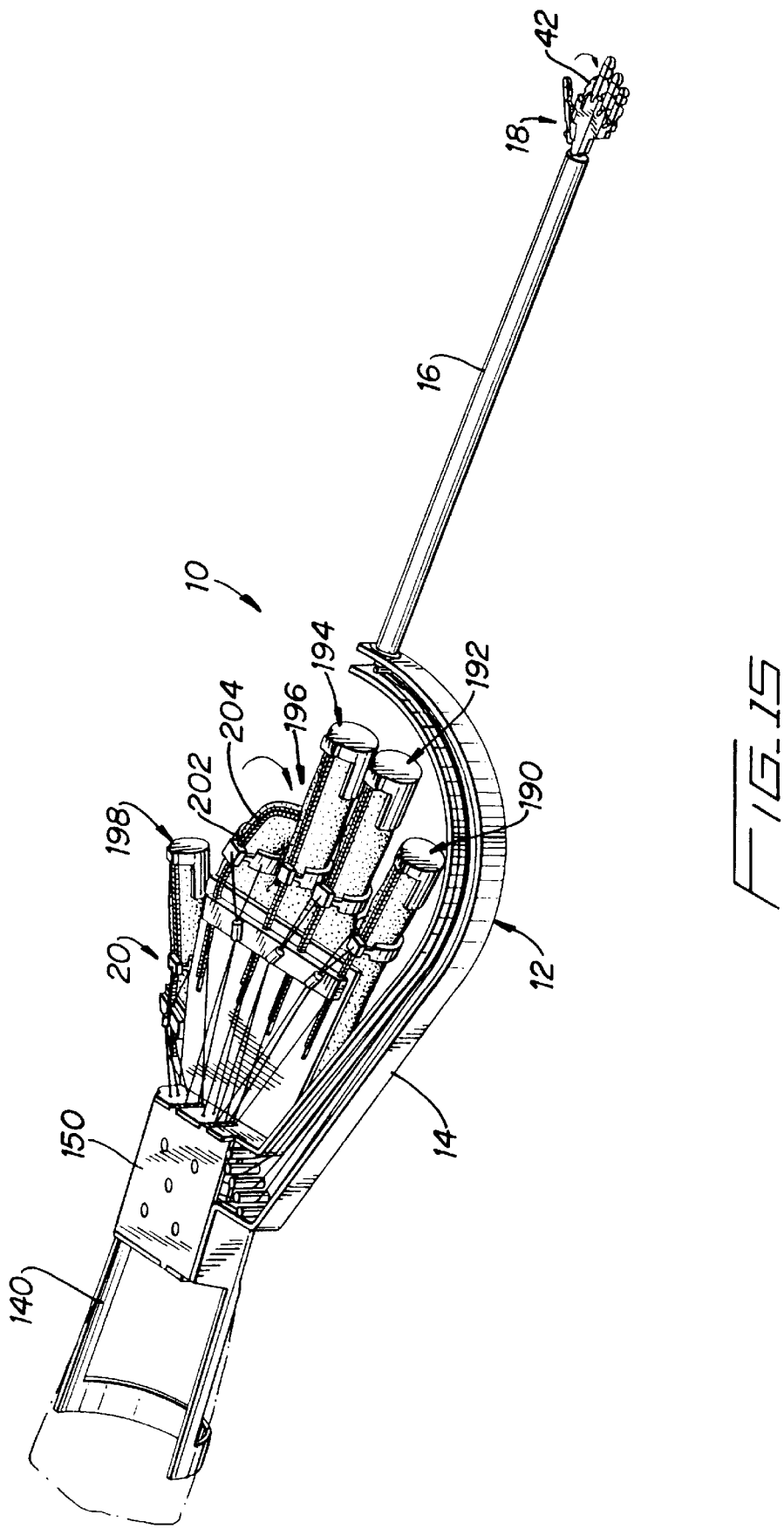

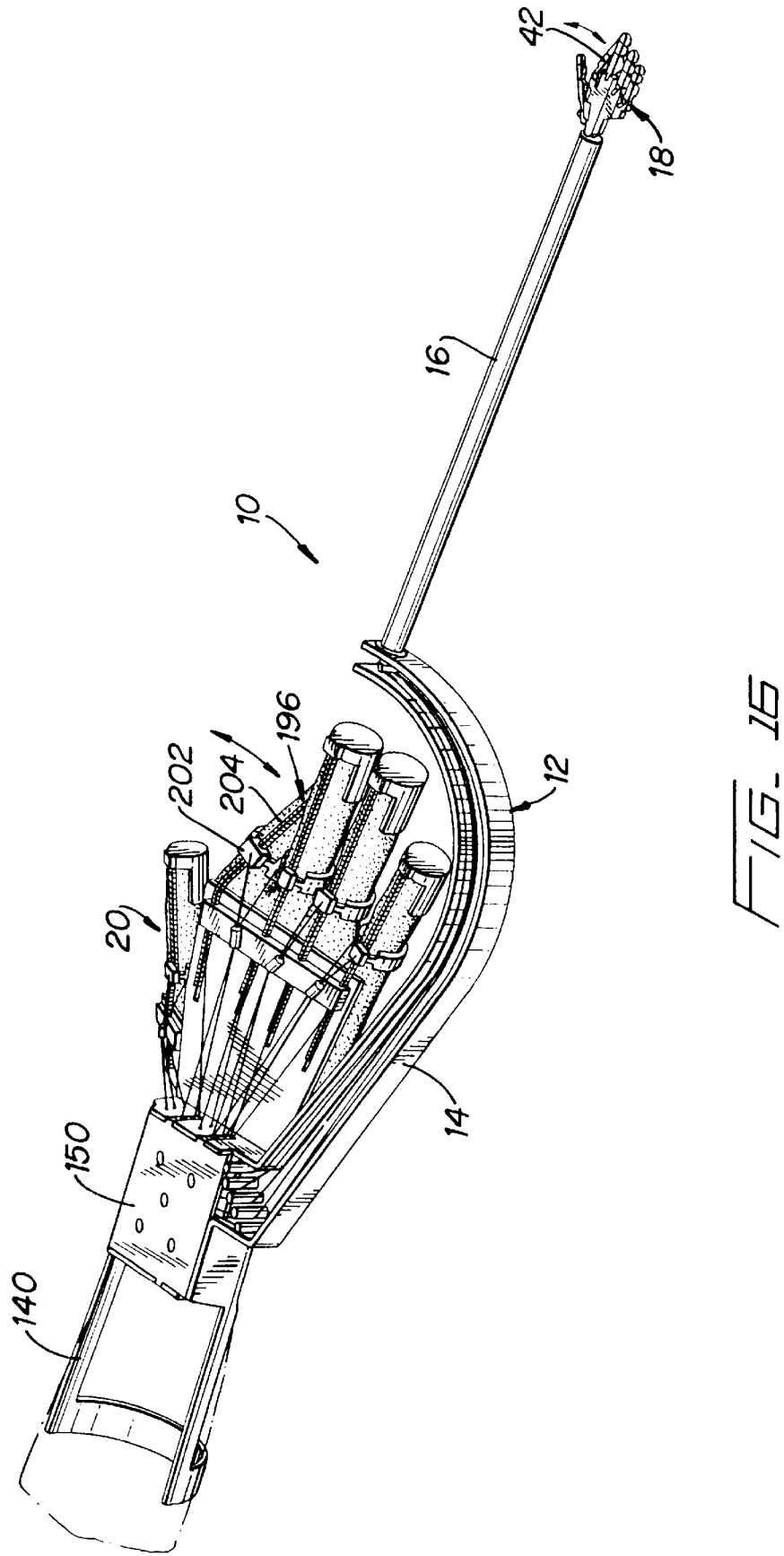

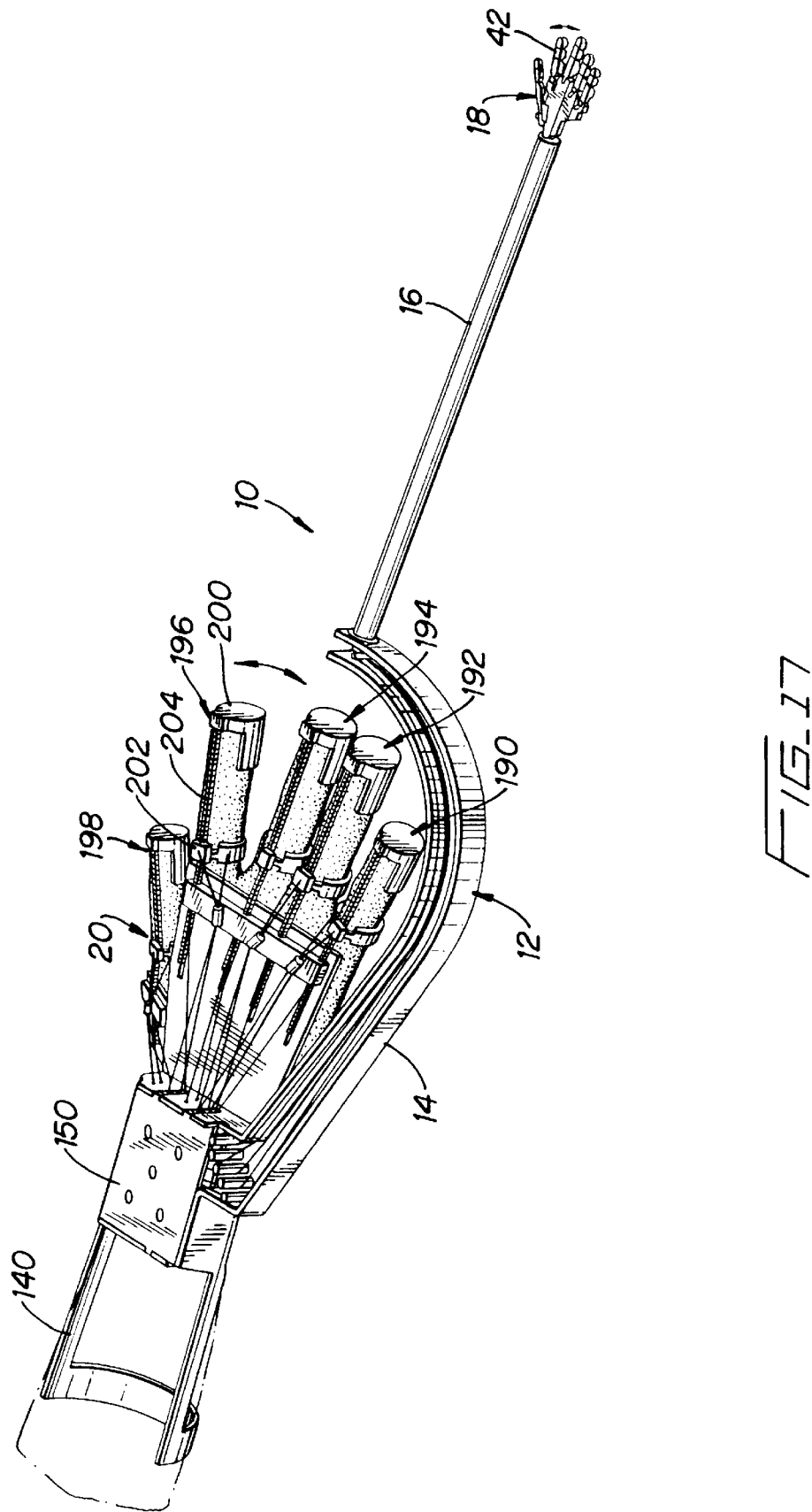

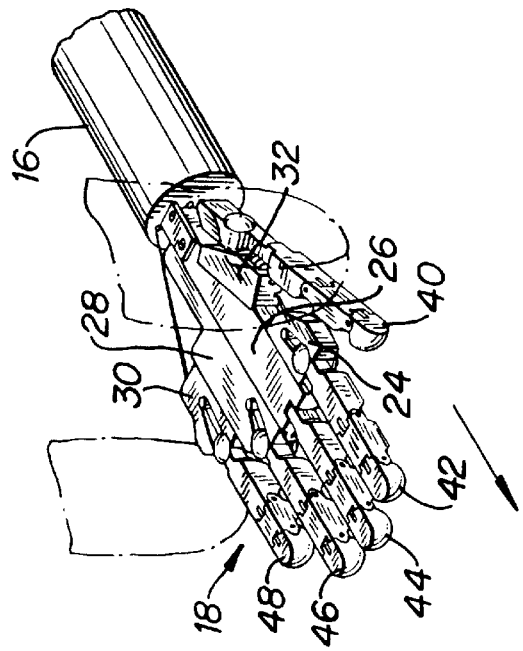
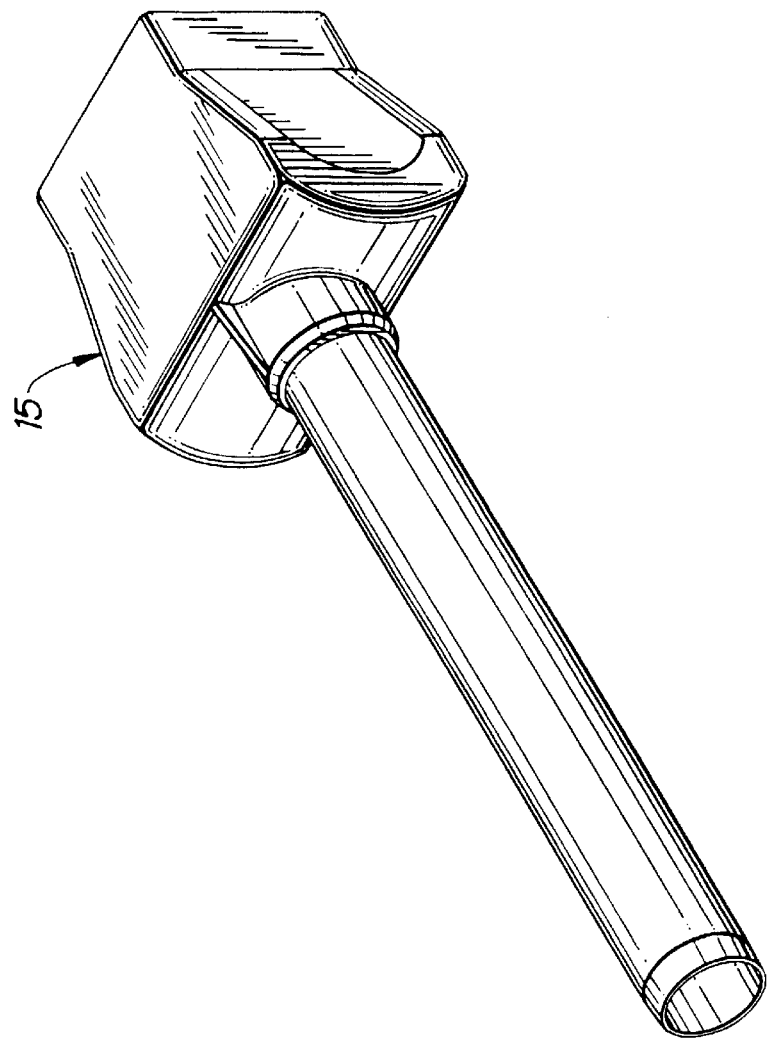
FIG. 18

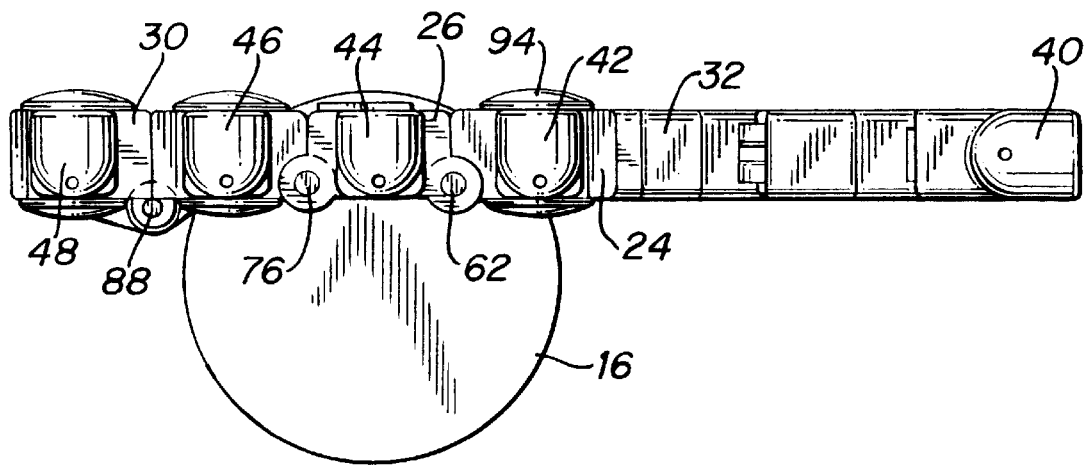
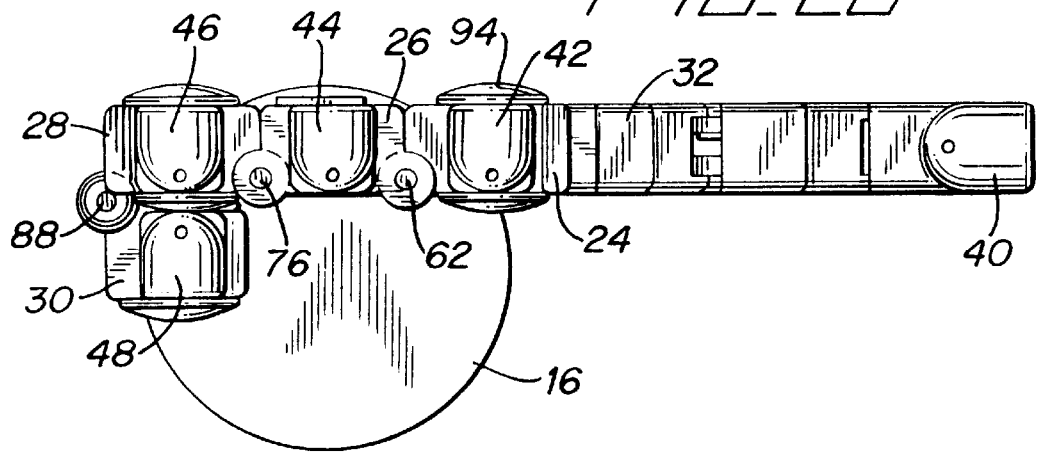
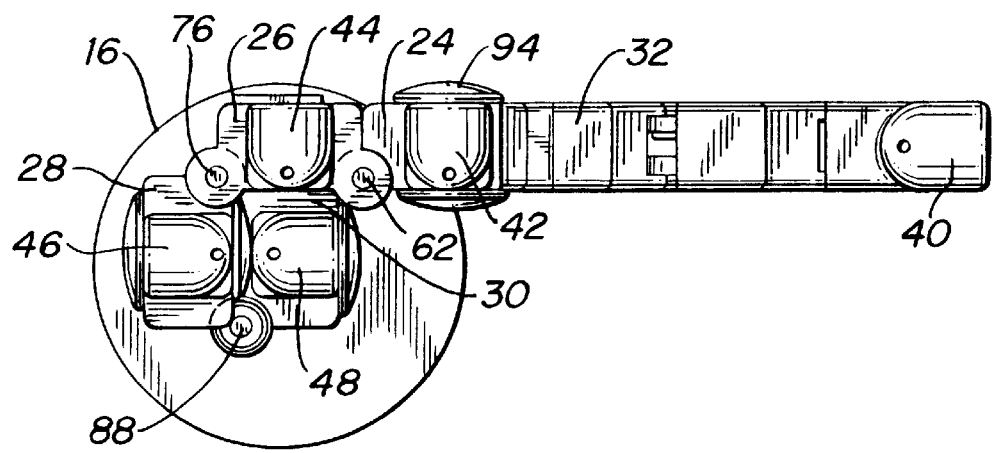

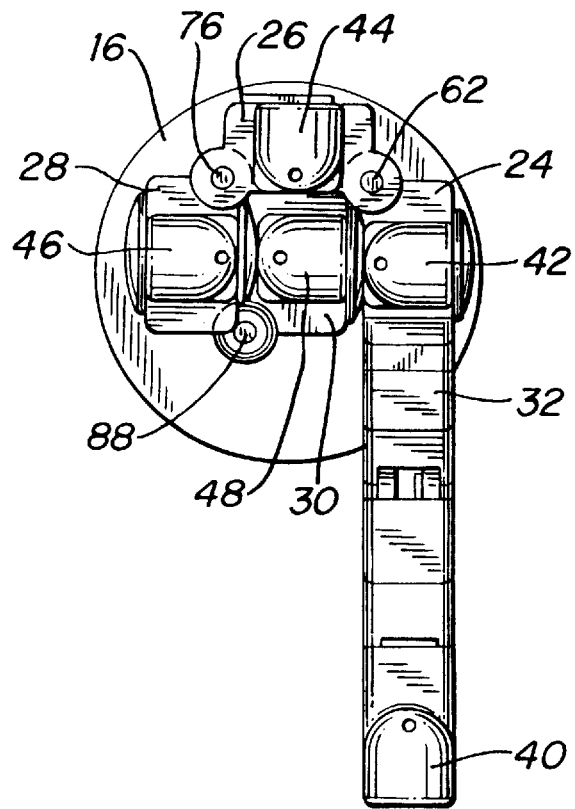
FIG_22
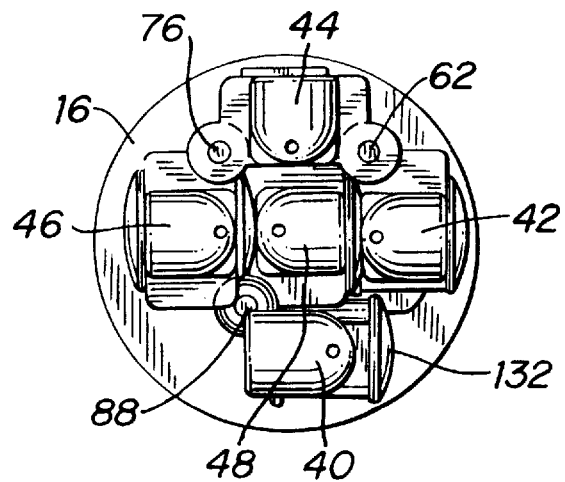
FIG_23

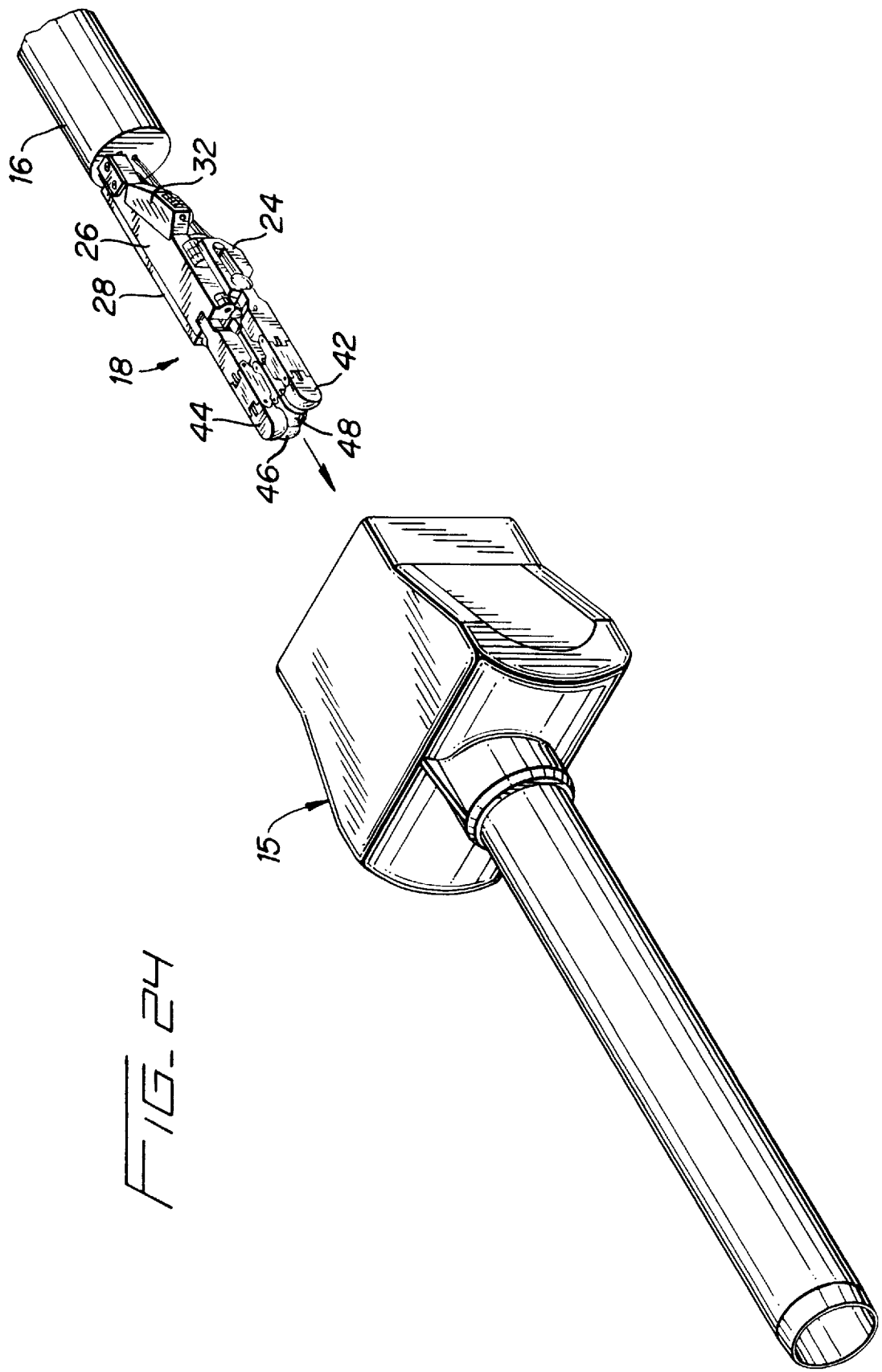

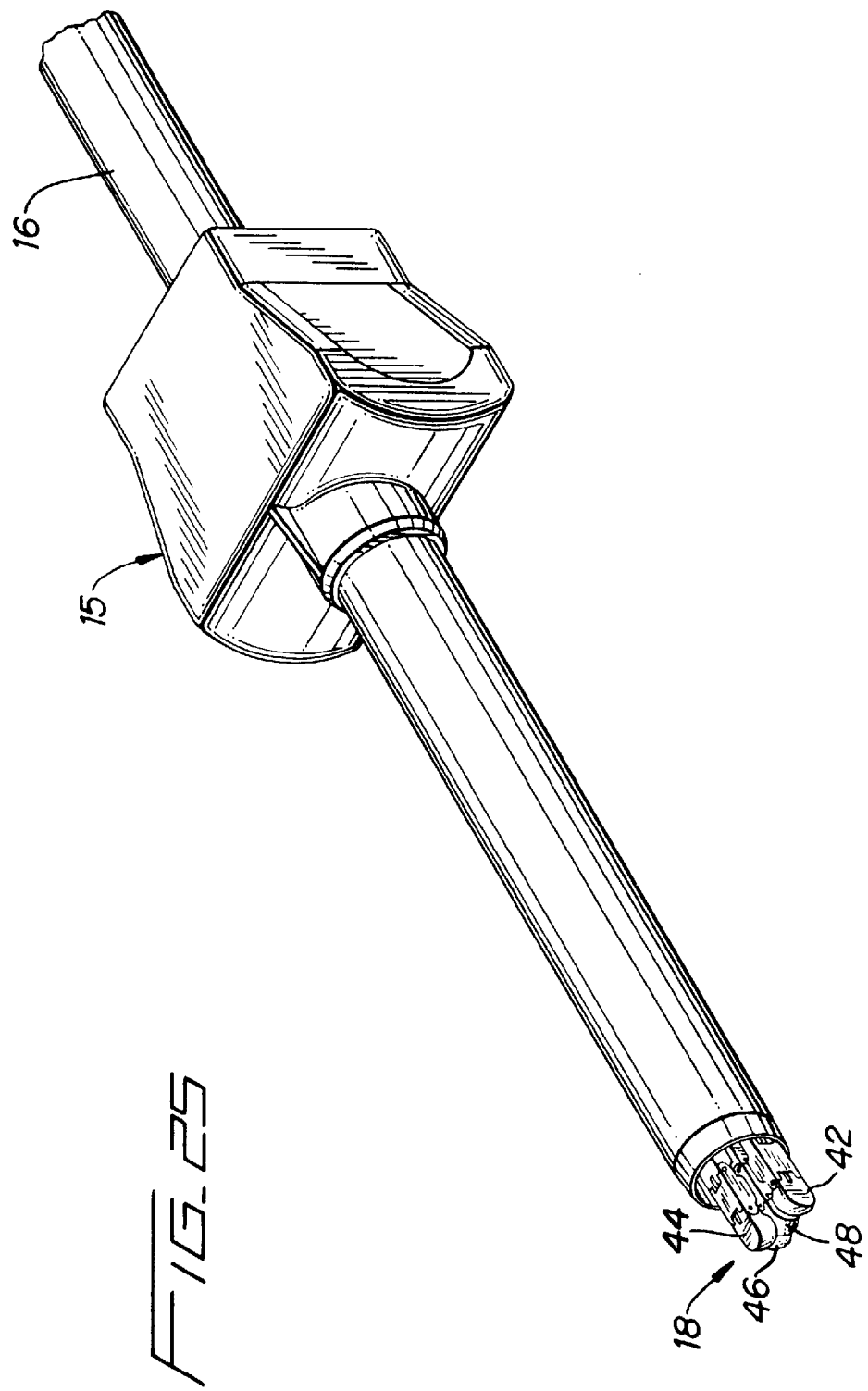

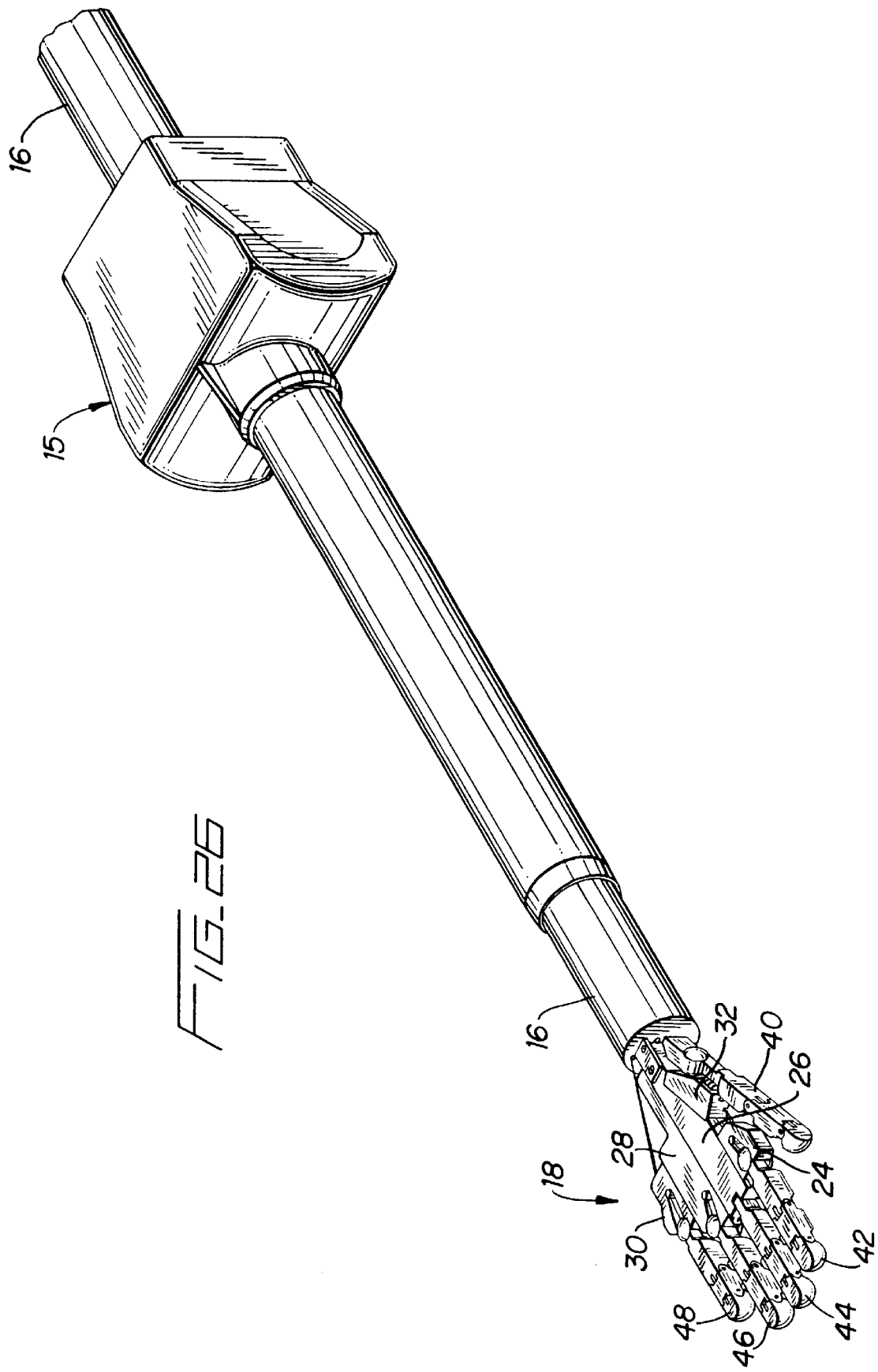

APPARATUS AND METHOD FOR PERFORMING SURGICAL TASKS DURING LAPAROSCOPIC PROCEDURES

This is a divisional of application Ser. No. 08/265,353 filed Jun. 24, 1994 (now abandoned).

BACKGROUND

1. Technical Field

An apparatus and method are provided for performing surgical tasks during laparoscopic procedures, and more particularly, a mechanical hand is provided which is configured to be introduced into the abdominal cavity and actuated from a remote location to perform a surgical task.

2. Description of Related Art

In laparoscopic and endoscopic surgical procedures, a small incision is made in the patient's body to provide access for a tube or cannula device. Once extended into the patient's body, the cannula allows insertion of various surgical instruments for acting on organs, blood vessels, ducts, or body tissue far removed from the incision. Such instruments include apparatus for applying surgical clips as disclosed in U.S. Pat. No. 5,084,057; apparatus for applying surgical staples as disclosed in U.S. Pat. Nos. 5,040,715 and 5,289,963; and apparatus for retracting body tissue as disclosed in U.S. Pat. No. 5,195,505.

In general, an endoscopic instrument has an elongated body with a tool assembly provided at the distal end thereof and an actuation assembly associated with the proximal end thereof for manipulating and actuating the tool assembly. Often, the degree of controlled manipulation of the tool assembly is limited by the position of the trocar or cannula device through which the particular instrument is extended, and the accessibility of the target tissue or organ to be acted upon.

It is recognized that it would be beneficial to provide a device capable of acting with the dexterity and mobility of a hand within the abdominal cavity to perform tasks during laparoscopic surgery. An example of a rudimentary hand-like device capable of gripping and manipulating tissue during endoscopic surgery is disclosed in German Patent No. DE 42 23 792. This device is limited, however, in its ability to perform more complex surgical tasks, such as, operating surgical instrumentation within the abdominal cavity while being controlled from a remote location.

SUMMARY

An apparatus for performing surgical tasks during laparoscopic procedures is provided. The apparatus includes an elongated body defining opposed proximal and distal portions, and a mechanical hand operatively associated with the distal portion of the elongated body which includes a plurality of movable fingers. An actuation assembly is operatively associated with the proximal portion of the elongated body and includes a plurality of digit control sub-assemblies each configured to receive an input signal from a user. Cable sets transmit the input signals from the digit control sub-assemblies to the fingers of the mechanical hand, and preferably the input signals imparted to the digit control sub-assemblies by the user are proportionally reduced.

In a preferred embodiment, the mechanical hand includes a hand portion including a plurality of hand sections hingedly connected to one another, a movable finger operatively associated with each of the hand sections, and an opposable thumb hingedly connected to one of the hand sections. Preferably, the opposable thumb and each of the hand sections of the mechanical hand are movable between a constrained position wherein the thumb and forehand sections are drawn together into a narrow formation to facilitate passage of the hand through a trocar or cannula device and a deployed position wherein the thumb and hand sections are spread out to facilitate performance of surgical tasks.

A plurality of cable sets are each configured to control the movement of a respective one of the movable fingers and opposable thumb. The cable sets include first, second and third control cables for independently controlling the movements of the proximal, medial, and distal phalangeal sections of the movable fingers. A plurality of pulley assemblies each corresponding to a respective one of the plurality of cable sets reduce the input signal.

Preferably, the actuation assembly includes a plurality of digit control sub-assemblies each corresponding to a respective one of the movable fingers and opposable thumb of the mechanical hand. Each of the digit control sub-assemblies includes a distal phalangeal engaging collar, a proximal phalangeal engaging ring, and an elongate support shaft for supporting the engaging collar and engaging ring. Preferably, a first control cable extends from the distal phalangeal collar and at least a second control cable extends from the proximal phalangeal engaging ring to facilitate flexion and extension of a respective one of the articulated fingers. A third control cable can be associated with the proximal engaging ring of the digit control assemblies to facilitate abduction and adduction of a respective one of the movable fingers and opposable thumb of the mechanical hand.

A method for performing a surgical task during a laparoscopic procedure is also disclosed including the steps of forming an incision in the peritoneum of a patient, extending a cannula device through the incision into the abdominal cavity of the patient, introducing a surgical instrument into the abdominal cavity through the cannula device, introducing a mechanical hand into the abdominal cavity through the cannula device, and manipulating the mechanical hand from a remote location to actuate the surgical instrument and thereby perform a surgical task.

BRIEF DESCRIPTION OF THE DRAWINGS

Various embodiments of the apparatus will be described hereinbelow with reference to the drawings wherein:

FIG. 1 is a perspective view of a surgical apparatus constructed in accordance with a preferred embodient with the mechanical hand oriented in a neutral position;

FIG. 2 illustrates a surgeon utilizing the apparatus of FIG. 1 in the performance of a laparoscopic surgical procedure;

FIG. 3A is an enlarged perspective view of the mechanical hand of the subject invention operating a surgical stapling device during the performance of a laparoscopic procedure;

FIG. 3B is an enlarged perspective view of the surgical stapling device illustrated in FIG. 3A;

FIG. 4 is an enlarged plan view of a mechanical hand constructed in accordance with a preferred embodiment;

FIG. 5 is a cross-sectional view taken along line 5—5 of FIG. 4 illustrating the construction of the proximal phalangeal joint of the index finger of the mechanical hand of FIG. 4;

FIG. 6 is an exploded perspective view of the mechanical hand of FIG. 4 with the elements of the hand separated for ease of illustration;

FIG. 7 is a cross-sectional view taken along line 7—7 of FIG. 4 illustrating the interior construction of index finger of the mechanical hand;

FIG. 8 is an exploded perspective view of the index finger of the mechanical hand illustrated in FIG. 4;

FIG. 9 is a cross-sectional view taken along line 9—9 of FIG. 4 illustrating the cable pathways extending through the mechanical hand;

FIG. 10 is a perspective view of the actuation assembly of the surgical apparatus of FIG. 1 illustrating the transmission assembly for manipulating the mechanical hand;

FIG. 13 is a cross-sectional view taken along line 13—13 of FIG. 1 illustrating the proximal phalangeal engagement ring of the index finger control sub-assembly;

FIG. 14 is a partial cross-sectional view taken along line 14—14 of FIG. 1 illustrating the proximal phalangeal engagement ring and the adjustable support shaft of the index finger control sub-assembly;

FIG. 15 is a perspective view of the surgical apparatus illustrated in FIG. 1, with the index finger of the mechanical hand disposed in a flexed position, articulated about the medial phalangeal joint thereof, in response to corresponding movement of the index finger control sub-assembly;

FIG. 16 is a perspective view of the surgical apparatus illustrated in FIG. 1, with the index finger of the mechanical hand disposed in a flexed position, articulated about the proximal phalangeal joint thereof, in response to corresponding movement of the index finger control sub-assembly;

FIG. 17 is a perspective view of the surgical apparatus illustrated in FIG. 1 with the index finger of the mechanical hand disposed in an abducted position in response to corresponding movement of the index finger control sub-assembly;

FIG. 18 is a perspective view of the mechanical hand and a trocar assembly prior to folding the hand into a constrained position for passage through the trocar assembly;

FIGS. 19-23 illustrate the sequence of steps in which the mechanical hand is folded into a constrained configuration for passage through the trocar assembly;

FIG. 24 is a perspective view of the mechanical hand folded in a constrained position for passage through a trocar assembly;

FIG. 25 is a perspective view of the mechanical hand passing through a trocar assembly; and FIG. 26 is a perspective view of the mechanical hand extending from a trocar assembly and disposed in a neutral position.

DETAILED DESCRIPTION OF THE PREFERRED EMBODIMENTS

Figure 11:
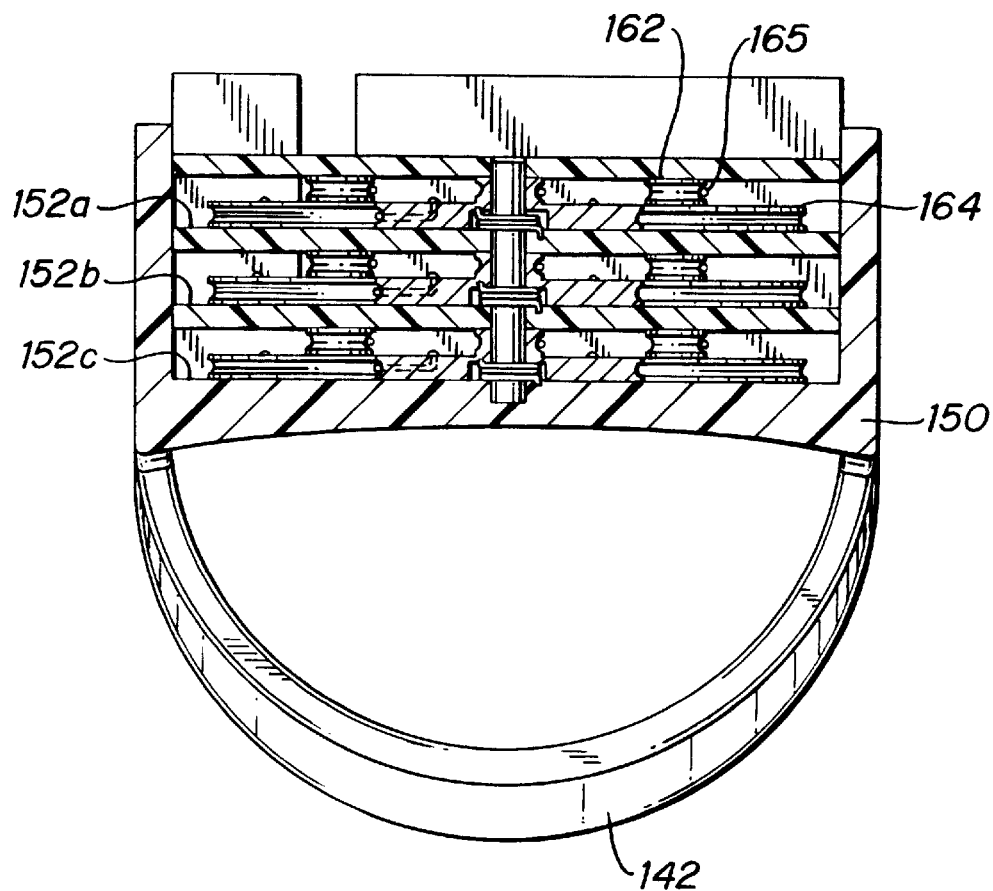
FIG. 11 is a cross-sectional view taken along line 11—11 of FIG. 1 illustrating the three levels of the transmission assembly of the actuation assembly.

The apparatus shall be discussed in terms of endoscopic procedures and apparatus. However, use herein of terms such as "endoscopic", "endoscopically", and "endoscopic portion", among others, should not be construed to limit the apparatus for use only in conjunction with an endoscopic tube. To the contrary, it is believed that the apparatus may find use in procedures wherein access is limited to a small incision including but not limited to arthroscopic and/or laparoscopic procedures.

Referring now to the drawings wherein like reference numerals indicate similar structural elements, there is illustrated in FIG. 1 an apparatus for performing surgical tasks during laparoscopic procedures which is constructed in accordance with a preferred embodiment and which is designated generally by reference numeral 10. Surgical apparatus 10 is particularly configured to perform complex surgical tasks within the abdominal cavity of a patient, such as operate surgical instrumentation, with a fine degree of dexterity and accuracy similar to that of an actual hand.

Referring to FIG. 1, surgical apparatus 10 includes a frame 12 having a proximal user interaction platform 14 and an elongated body 16 which extends from user interaction platform 14. The elongated body preferably has a diameter of between about 5 and about 15 mm and a length of between about 10 inches and 12 inches for insertion through a trocar cannula. Clearly other dimensions are contemplated. A mechanical hand 18 having five movable fingers extends from a distal end of elongated body 16. An actuation assembly 20 is operatively associated with interaction platform 14 for manipulating and controlling the movements of mechanical hand 18. The user interaction platform 14 and the mechanical hand 18 are in alignment with one another to promote user comfort and a favorable operating position. Mechanical hand 18 is preferably one fourth the size of a human hand and is preferably configured to function in substantially the same manner as a human hand. As will be described in detail below, actuation assembly 20 includes five control fingers which, upon movement, cause corresponding movements of the five fingers of mechanical hand 18.

Referring to FIG. 2, during a laparoscopic procedure, the hand of the surgeon is placed within actuation assembly 20 such that each of his/her fingers fits into a respective reception area of the actuation assembly 20. That is, each of the surgeon's fingers fits into the corresponding finger support of glove 199 as described below. The elongate body 16 of frame 12 is inserted through a trocar 15, and the mechanical hand 18 is employed to perform a particular surgical task, such as operating a fastener applying device 17, as illustrated in FIG. 3A. Fastener applying device 17 is illustrated in FIG. 3B and includes an elongate body 17a having a fastener applying assembly 17b at the distal end thereof and a controller 17c at the proximal end thereof. During the performance of a surgical procedure, the fingers of the mechanical hand 18 will advantageously respond to each movement of the surgeon's fingers positioned within actuation assembly 20. Preferably, the surgeon will operate two of these mechanical hands and will view the procedure on a video monitor or through a laparoscope introduced into the abdominal cavity.

Referring now to FIGS. 4 and 5, the mechanical hand 18 includes hand portion 22 which includes a plurality of hingedly connected hand sections each having associated therewith a respective finger. In particular, hand portion 22 includes an inner hand section 24, a first medial hand section 26, a second medial hand section 28, and an outer hand section 30. The relative positions of hand sections 24-30 correspond substantially to the relative positions of the second through fifth metacarpal bones of the human hand. Hand portion 22 further includes a proximal hand section 32 corresponding to the first metacarpal bone of the human hand which is associated with the thumb.

Proximal hand section 32 depends angularly from the first medial section 26 of hand portion 22. The inner hand section 24 and second medial section 28 of hand portion 22 are hingedly connected to hand section 26. The outer hand section 30 is hingedly connected to the minor medial section 28. The proximal end of the major medial hand section 28 is configured to be fastened to a flange 34 which extends distally from the elongated body 16 of frame 12 to support mechanical hand 18.

Referring to FIG. 6, the mechanical hand 18 is illustrated with each of the hand sections thereof and their respective fingers separated from one another for ease of illustration. The five fingers of mechanical hand 18 include digit 40 which corresponds to the thumb, digit 42 which corresponds to the index finger 42, digits 44 and 46 which correspond to the middle and ring fingers respectively, and digit 48 which corresponds to the little finger.

The first medial hand section 26 of hand portion 22 is generally rectangular in configuration and defines opposed lateral surfaces 26a and 26b and opposed distal and proximal end portions 26c and 26d. Proximal end portion 26d is provided with a pair of spaced apart apertures 36a and 36b for respectively receiving fasteners 38a and 38b for mounting hand section 26 to flange 34. The proximal hand section 32 depends angularly from the lateral surface 26b of hand section 26 and has a cavity 50 formed therein for receiving hinging flanges 52a and 52b provided on the metacarpal portion of thumb 40. A pin 54 extends through section 32 and longitudinally through flanges 52a, 52b to fasten thumb 40 to hand section 32 and a coiled torsion spring 56 biases thumb 40 into an outwardly spread position.

The inner hand section 24 of hand portion 22 has distal and proximal hinging flanges 58a and 58b provided thereon for interfitting with corresponding distal hinging flange 60a and proximal hinging flanges 60b and 60c provided on lateral surface 26b of hand section 26 (see FIG. 4). Hinge pins 62 and 63 are provided to fasten hand section 24 to hand section 26 and a coiled torsion spring 64 is provided for biasing hand section 24 into a normally spread position.

The second medial hand section 28 includes a distal hinging flange 70 and a proximal hinging flange 72 for interfitting with distal and proximal hinging flanges 74 and 76 which depend from lateral surface 26b of hand section 26 (see FIG. 4). Proximal and distal hinge pins 78 and 76 fasten forehand sections 26 and 28 to one another and a coiled torsion spring 82, associated with proximal hinge pin 78, biases the two hand sections into an outwardly spread position.

The outer hand section 30 has spaced apart hinging flanges 84a and 84b for interengaging corresponding hinging flanges 86a and 86b which are formed in hand section 28 (see FIG. 4). Hand sections 28 and 30 are fastened to one another by a hinge pin 88 and a coiled torsion spring 90 biases the two hand sections into an outwardly spread configuration.

The hinging of each of the sections of hand portion 22 facilitates the relative movement of the hand sections between a normally outstretched or open position (also referred to herein as the neutral position), shown for example in FIG. 18, and a narrow constrained position, shown for example in FIG. 24, to enable passage of mechanical hand 18 through a cannula or trocar assembly and into the abdominal cavity of a patient. A sequence of steps by which each of the hand sections and fingers of mechanical hand 18 are manipulated or folded into a narrow constrained position is described in detail hereinbelow with reference to FIGS. 19–23. The movement of the fingers from the neutral position to various operating positions for use during a surgical procedure is also described below.

With continued reference to FIGS. 4 and 6, the five fingers of mechanical hand 18 are each associated with a respective one of the sections of hand portion 22. Digit 42 (the index finger) is operatively connected to the inner forehand section 24. A cylindrical cavity 92 is defined in forehand section 24 for receiving a cylindrical barrel joint 94 provided at the proximal end of digit 42. Barrel joint 94 enables abduction and adduction of digit 42 (see generally FIG. 17). A groove 96 is also formed in hand section 24 and depends proximally from cavity 92 to support a coiled torsion spring 98 mounted about an upstanding post 100. Spring 98 serves as a return spring to bias digit 42 toward its normal position when it is abducted or adducted during the performance of a surgical task.

Digit 44 is operatively connected to the first medial section 26 by a transverse hinge pin 128. Digits 46 and 48 are operatively connected to hand sections 28 and 30 respectively by seating the respective barrel joints 47 and 49 thereof within corresponding reception cavities 29 and 31 formed in hand sections 28 and 30. Torsion springs 95 and 97 serve as return springs to bias digits 46 and 48 toward their normal positions when they are abducted or adducted about barrel joints 47 and 49 during the performance of a surgical procedure.

Referring now to FIGS. 7–9, digit 42 is illustrated and exemplifies the construction of the fingers of mechanical hand 18. Digit 42 includes distal, medial, and proximal phalangeal sections 102, 104, and 106. Proximal section 106 is pivotably engaged to barrel joint 94. Barrel joint 94 defines an interior cavity 94a for receiving posterior hinging flanges 107a and 107b provided on proximal phalangeal section 106. A hinge pin 108 fastens the proximal section 106 and barrel joint 94 to one another and enables flexion and extension of digit 42 during the performance of a surgical task (see generally FIG. 16). A coiled torsion spring 110 is disposed about hinge pin 108 and acts to return digit 42 to its normally longitudinal position following the flexion or extension thereof.

Anterior hinging flanges 112a and 112b are provided on proximal phalangeal section 106 for interengaging corresponding posterior hinging flanges 114a and 114b on medial phalangeal section 104. A hinge pin 116 fastens the proximal and medial phalangeal sections 106 and 104 to one another and a torsion spring 118 biases section 104 into its normal position in longitudinal alignment with section 108. Anterior hinging flanges 120a and 120b are also provided on medial section 104 for interengaging corresponding hinging flanges 122a and 122b on distal phalangeal section 106 of digit 42. The distal and medial sections 102 and 104 are fastened to one another by hinge pin 124 and are biased into longitudinal alignment (i.e. the position of FIG. 7) by torsion spring 126.

Referring again to FIGS. 4 and 6, digits 46 and 48, with the exception of size are substantially identical in construction to digit 42. Digit 44, which corresponds to the middle finger, differs in construction in that it does not include a barrel joint for abduction and adduction as described above with respect to digit 42. Digit 44 can only be extended or flexed about hinge pin 128 which as noted above fastens the proximal phalangeal section 130 of digit 44 to the distal portion 26c of hand section 26. Digit 44 is intended to be utilized to palpate organs or body tissue and the construction thereof is particularly adapted for such tasks. It is also contemplated however, that alternatively digit 44 can be mounted to hand portion 22 by a barrel joint connection for movement in the manner described above with respect to digit 42.

Digit 40, the thumb, as described above, includes a lateral hinging joint (52*a*, 52*b*) to facilitate the extension and flexion thereof. Digit 40 further includes a transverse barrel joint 132 located proximal of the lateral hinging joint (52*a*, 52*b*) and positioned to facilitate extension and flexion of the thumb. An exterior torsion spring 134 is associated with digit 40 and is mounted on an outwardly extending post 136 for biasing the thumb into an extended position. Digit 40 also flexes about its distal, medial, and proximal phalangeal sections in a direction transverse to the direction of flexure of digits 42–48. That is, digit 40 flexes toward section 26 and the remaining digits flex downwardly. Such movements enable complete opposition of digit 40 and the other fingers of mechanical hand 18.

Referring now to FIG. 10, in conjunction with FIG. 1, the user interaction platform 14 of frame 12 includes a cuff 140 for supporting the user's forearm. Cuff 140 includes an arcuate brace 142 and elongate support struts 144 and 146. Support struts 144 and 146 extend proximally from a generally rectangular transmission box 150. Transmission box 150 houses a plurality of pulley assemblies, 152, 154, 156, 158, and 160, which provide means to reduce the input signals generated by the user and transmitted to the mechanical hand 18 by a plurality of control cables during the performance of a surgical task.

As best seen in FIG. 11, each of the pulley assemblies 152–160 in transmission box 150 include three tiers of reduction pulleys, with each tier including an input pulley and an output pulley. For example, pulley assembly 152 includes three tiers of reduction pulleys 152*a*, 152*b*, and 152*c*, with each tier of the pulley assembly including an input pulley 162 and an output pulley 164. The diameter of each output pulley is preferably four times greater than the diameter of each input pulley to achieve the desired one fourth reduction in the input signal transmitted by the control cables. Thus, for example, when the surgeon flexes his/her index finger, the corresponding digit of mechanical hand 18 will move in the same manner through a distance equal to one fourth the distance the user's finger is moved. Other pully diameters are contemplated if a different input signal reduction is required.

Figure 12:
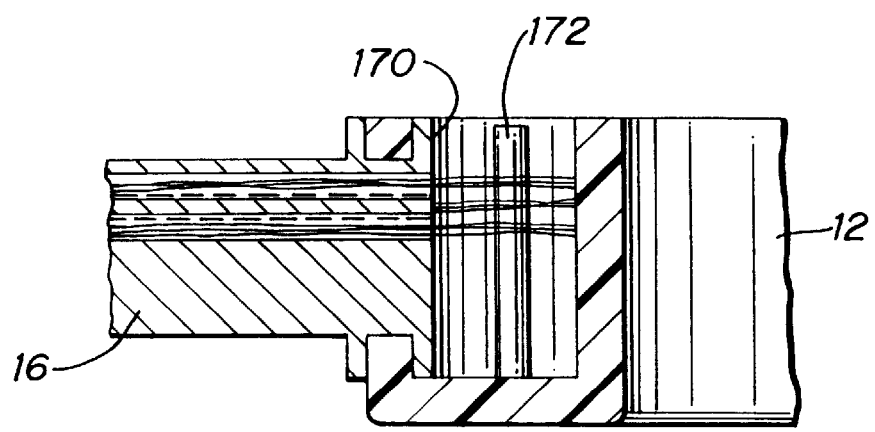
FIG. 12 is a cross-sectional view taken along line 12—12 of FIG. 1 illustrating the entrance port of the elongate body portion of the surgical apparatus.

Referring to FIGS. 10 and 11, a control cable extending from actuation assembly 20 into transmission box 150, for example control cable 165, is initially directed around input pulley 162, and led around output pulley 164 (as shown in FIG. 11), and directed about a primary orienting post 166 toward a secondary orienting post 168 (as shown in FIG. 10). Cable 165 is then led through a curved cable track 170, about a main orienting post 172, and into the elongate body 16 of frame 12, as illustrated in FIG. 12. A cover 178 is also provided for enclosing transmission box 150 to protect the pulley assemblies and control cables therein, as is a cover 179 for protecting cable track 170.

With continued reference to FIG. 10, in conjunction with FIG. 1, actuation assembly 20 includes a support plate 182 which extends distally from transmission box 150, a plurality of digit control sub-assemblies 190–198 adjustably mounted to support plate 182, and a form-fitting glove 199 for cladding the user's hand.

As best seen in FIG. 1, each of the digit control sub-assemblies 190–198 corresponds to a respective one of the user's fingers and accordingly, a respective one of the fingers of mechanical hand 18. Each digit control sub-assembly includes three operative elements. For example, sub-assembly 194 includes a distal phalangeal engagement collar 200, a proximal phalangeal engagement ring 202, and an elongate flexible support shaft 204 upon which engagement collar 200 and engagement ring 202 are mounted. The elements of the digit control sub-assemblies are illustrated in greater detail in FIGS. 13 and 14. In particular, support shaft 204 includes a plurality of spaced apart teeth 206 for permitting selective positioning of engagement ring 202. This feature enables the sub-assemblies to be adjusted to accommodate different users. The other sub-assemblies of actuation assembly 20 include the same three operative elements (i.e. engagement collar, engagement ring, and flexible support shaft) and for clarity are not specifically labeled in the drawings.

As best seen in FIG. 13, engagement ring 202 includes a mounting block 208 through which extends an axial slot 210 for receiving support shaft 204 and within which is disposed a deflectable locking tab 212 for selectively engaging the teeth 206 on support shaft 204. A pair of arcuate ring portions 214*a* and 214*b* are deflectably connected to mounting block 208 and include respective toothed engagement areas 215*a* and 215*b* for adjusting the diameter of ring 202 to accommodate the user.

Referring to FIG. 1, as noted above, the sub-assemblies of actuation assembly 20 are each associated with a plurality of control cables which provide means for transmitting the input signals from the digit control subassemblies 190–198 to the articulated fingers 42–48 and opposable thumb 40 of mechanical hand 18. Each of the sub-assemblies, with the exception of that which corresponds to digit 44 of mechanical hand 18, has three control cables associated therewith. Since digit 44 is not configured for abduction and adduction, a third control cable is excluded from the corresponding control sub-assembly. However, as noted above, alternately digit 44 can include a third control cable of abduction/adduction is desirable.

In general, as illustrated in FIG. 1, of the three control cables associated with each digit control sub-assembly, a first control cable extends from the distal phalangeal collar 200, and second and third control cables extend from the proximal phalangeal ring 202 of each sub-assembly (see FIG. 14). The first control cable of each sub-assembly controls articulation of the distal phalangeal section of the digit of the mechanical hand with which it is associated (see generally FIG. 15). The second control cable controls flexion and extension of the particular digit of the mechanical hand about the hinge pin which connects the digit to the forehand (see generally FIG. 16). The third control cable controls abduction and adduction of the particular digit of the mechanical hand about the barrel joint which connects the digit to the forehand (see generally FIG. 17).

Referring to FIGS. 6–9, by way of example, digit 42 of mechanical hand 18 is shown to illustrate the attachment points of the control cables particularly associated therewith. A first control cable 220 extending from actuation assembly 20 is fastened to the distal phalangeal section 106 of digit 42 by a connective fitting 221. Second and third control cables 222 and 224 extending from actuation assembly 20 are fastened to the proximal phalangeal section 102 of digit 42 by connective fittings 223 and 225 (see FIG. 4). Control cable 222 is fastened adjacent the centeroidal axis of the phalangeal section for effecting flexion and extension, while cable 224 is fastened adjacent a lateral portion thereof for effecting abduction and adduction. Digit 40, 44, 46, and 48 each include control cables attached at similar locations on their respective digital and proximal phalangeal sections. These control cables are illustrated in FIG. 6 but are not specifically labeled for clarity. As illustrated in FIG. 9, axial pathways 226 are formed in each section of hand portion 22 to direct the control cables to the particular finger associated therewith.

As noted above, the structural elements of the mechanical hand are particularly adapted to be manipulated from a normally out-spread position, shown for example in FIG. 18, to a narrow constrained position, shown for example in FIG. 24, to facilitate passage of mechanical hand 18 through trocar 15, as illustrated in FIGS. 25–26. The sequence in which the various structural elements of mechanical hand 18 are manipulated from an out-spread position to a constrained position is illustrated in FIGS. 19–23. The circular cross-section of trocar assembly 15 is represented in FIGS. 19–23 to provide a frame of reference for the manipulation sequence.

Initially, prior to extending mechanical hand 18 through trocar assembly 15, the outer hand section 30 of hand portion 22 is pivoted from the neutral position shown in FIG. 19 to a position disposed beneath second medial section 28, as shown in FIG. 20. Then, in conjunction, sections 28 and 30 are pivoted relative to first medial section 26, as shown in FIG. 21. Subsequently, as illustrated in FIG. 22, the inner hand section 24 is pivoted relative to first medial section 26 to a position in alignment with hand sections 28 and 30. The opposable thumb 40 is then manipulated twice to complete the sequence. First, thumb 40 is pivoted about hinge pin 54 and then it is flexed inwardly about barrel joint 132 into the position shown in FIG. 23. At such a time, mechanical hand 18 will be in the constrained position depicted in FIG. 24. Thereupon, mechanical hand 18 can be introduced into trocar assembly 15 and extended therethrough as shown in FIG. 25. When mechanical hand 18 is fully inserted to extend from the distal end of trocar assembly 15, the various spring biased structural elements thereof will return to their normally out-stretched orientations, as shown in FIG. 26, and mechanical hand 18 will be ready to perform surgical tasks as illustrated in FIG. 3. In particular, torsion spring 56 biases digit 40 into its normal position, torsion spring 64 biases hand section 24 into its normal position, torsion spring 82 biases sections 26 and 28 into their normal position, and torsion spring 90 biases section 30 into its normal position.

In use, once the surgeon has placed his/her hand in glove 199, he/she can perform a wide range of surgical tasks. For example, by actuating the middle finger control sub-assembly of actuation assembly 20 through flexion or extension of his/her own middle finger, digit 44 will flex and extend in the same manner to palpate organs or body tissue within the abdominal cavity. To perform more complex tasks, such as operating a stapling device, as illustrated in FIG. 3A, the user will orient his/her hand into a suitable position wherein mechanical hand 18 can grasp stapling device 17. Once grasped, the instrument can be actuated by the surgeon through movement of his/her thumb in such a manner so as to cause digit 40 of mechanical hand 18 to depress the control assembly 17c of stapling device 17 to staple body tissue.

Although the apparatus has been described with respect to preferred embodiments, it will be readily apparent to those having ordinary skill in the art to which it appertains that changes and modifications may be made thereto without departing from the spirit or scope of the appended claims.

What is claimed is:

1. An apparatus for performing surgical tasks during laparoscopic procedures comprising:
   a) an elongated body defining a longitudinal axis and opposed proximal and distal portions;
   b) a mechanical hand operatively associated with the distal portion of the elongated body and including a plurality of movable fingers, the mechanical hand including a plurality of hand sections connected to one another by hinges, the hand sections being pivotable around the hinges along respective axes which are parallel to the longitudinal axis of the elongated body;
   c) an actuation assembly operatively associated with the proximal portion of the elongated body and including a plurality of digit control sub-assemblies each configured to receive an input signal from a user;
   d) means for transmitting the input signals from the digit control sub-assemblies to the movable fingers of the mechanical hand; and
   e) means operatively associated with the signal transmitting means for proportionally reducing the input signal imparted to the digit control sub-assemblies by the user.

2. An apparatus as recited in claim 1, wherein each hand section has associated therewith a respective one of the plurality of movable fingers.

3. An apparatus as recited in claim 2, wherein one of the hand sections has an opposable thumb associated therewith.

4. An apparatus as recited in claim 2, wherein each of the movable fingers includes respective proximal, medial, and distal phalangeal sections and wherein at least one of the movable fingers includes a proximal joint connecting the proximal phalangeal section thereof to a respective hand section and configured to facilitate adduction and abduction of the finger.

5. An apparatus as recited in claim 2, wherein each of the movable fingers includes respective proximal, medial and distal phalangeal sections at least one of the movable fingers includes a proximal joint connecting the proximal phalangeal section thereof to a respective hand section and configured to facilitate flexion and extension of the finger.

6. An apparatus as recited in claim 2, wherein each of the movable fingers includes respective proximal, medial and distal phalangeal sections and the signal transmitting means corresponding to at least one of the movable finger comprises first, second, and third control cables for independently controlling the articulated movements of the proximal, medial and distal phalangeal sections thereof.

7. An apparatus as recited in claim 1, wherein the signal transmitting means comprises a plurality of cable sets each configured to control the movement of a respective one of the movable fingers of the mechanical hand.

8. An apparatus as recited in claim 7, wherein the input signal reducing means comprises a plurality of pulley assemblies each corresponding to a respective one of the plurality of cable sets.

9. An apparatus as recited in claim 8, wherein the input signal reducing means is configured to proportionally reduce the input signal at a ratio of about 1 to 4.

10. An apparatus as recited in claim 1, wherein the hand sections of the mechanical hand are configured to move between a constrained position wherein the hand sections are drawn together to facilitate passage of the mechanical hand through a trocar assembly and a deployed position wherein the hand sections are spread to facilitate performance of a surgical task.

11. An apparatus for performing surgical tasks during laparoscopic procedures comprising:
   a) an elongated body defining opposed proximal and distal portions:
   b) a mechanical hand operatively associated with the distal portion of the elongated body and including a plurality of movable fingers, wherein the mechanical hand comprises a hand portion including a plurality of hand sections hingedly connected to one another, the hand sections being configured to move between a constrained position wherein the hand sections are drawn together to facilitate passage of the mechanical hand through a trocar assembly and a deployed position wherein the hand sections are spread to facilitate performance of a surgical task, wherein the hand sections are spring biased into the deployed position;
   c) an actuation assembly operatively associated with the proximal portion of the elongated body and including a plurality of digit control sub-assemblies each configured to receive an input signal from a user:

d) means for transmitting the input signals from the digit control sub-assemblies to the movable fingers of the mechanical hand; and e) means operatively associated with the signal transmitting means for proportionally reducing the input signals imparted to the digit control sub-assemblies by the user.

12. An apparatus for performing surgical tasks during laparoscopic procedures comprising:

a) an elongated body defining opposed proximal and distal portions:

b) a mechanical hand operatively associated with the distal portion of the elongated body and including a plurality of movable fingers, wherein each of the digit control sub-assemblies includes a distal phalangeal engaging collar, a proximal phalangeal engaging ring, and an elongate support shaft for supporting the engaging collar and engaging ring;

c) an actuation assembly operatively associated with the proximal portion of the elongated body and including a plurality of digit control sub-assemblies each configured to receive an input signal from a user;

d) means for transmitting the input signals from the digit control sub-assemblies to the movable fingers of the mechanical hand; and e) means operatively associated with the signal transmitting means for proportionally reducing the input signal imparted to the digit control sub-assemblies by the user.

13. An apparatus as recited in claim 12, wherein the signal transmitting means includes a first control cable extending from the distal phalangeal engaging collar, and at least a second control cable extending from the proximal phalangeal engaging ring to facilitate flexion and extension of a respective one of the movable fingers.

14. An apparatus as recited in claim 13, wherein the signal transmitting means associated with at least one of the digit control sub-assemblies includes a third control cable to facilitate abduction and adduction of a respective one of the movable fingers.

15. An apparatus for performing surgical tasks during laparoscopic procedures comprising:

a) a frame including an elongated body extending distally therefrom;

b) a mechanical hand operatively associated with a distal end portion of the elongated body and including a plurality of movable fingers; and c) an actuation assembly operatively associated with the mechanical hand for controlling the operation thereof including:

i) a plurality of movable control fingers each corresponding to a respective one of the movable fingers of the mechanical hand;

ii) a set of control cables extending from each of the control fingers to a respective one of the movable fingers of the mechanical hand for transmitting input signals; and iii) a set of pulleys operatively associated with each set of control cables for proportionally reducing the input signals imparted thereto.

16. An apparatus as recited in claim 15, wherein the mechanical hand comprises a hand portion including a plurality of hand sections hingedly connected to one another.

17. An apparatus as recited in claim 16, wherein each hand section has associated therewith a respective one of the plurality of movable fingers.

18. An apparatus as recited in claim 16, wherein the mechanical hand includes an opposable thumb associated with one of the hand sections.

19. An apparatus as recited in claim 15, wherein the set of control cables includes a first and second control cable to facilitate flexion and extension of a respective one of the movable fingers of the mechanical hand and third control cable to facilitate abduction and adduction of a respective one of the movable fingers.

20. An apparatus as recited in claim 18, wherein the input signal reducing means is configured to proportionally reduce the input signal at a ratio of about 1 to 4.

21. A mechanical hand for use during laparoscopic surgical procedures comprising:

a) a hand portion including a plurality of hand sections hingedly connected to one another, b) an articulated finger operatively associated with each of the hand sections; and c) an opposable thumb hingedly mounted to one of the hand sections, whereby the opposable thumb and each of the hand sections are movable between a constrained position wherein the thumb and hand sections are drawn together into a narrow formation to facilitate passage of the hand through a trocar and a deployed position wherein the thumb and hand sections are spread out to facilitate performance of surgical tasks.

22. An apparatus as recited in claim 21, wherein each of the articulated fingers includes a respective proximal, medial, and distal phalangeal section.

23. An apparatus as recited in claim 22, wherein at least one of the articulated fingers includes a proximal joint connecting the proximal phalangeal section thereof to a respective forehand section and configured to facilitate adduction and abduction of the finger.

24. An apparatus as recited in claim 21, wherein at least one of the articulated fingers includes a proximal joint connecting the proximal phalangeal section thereof to a respective forehand section and configured to facilitate flexion and extension of the finger.

25. An apparatus for performing surgical tasks during laparoscopic procedures comprising:

a) an elongated body defining a longitudinal axis;

b) a first hand extending from a distal end portion of the elongated body and having a plurality of movable fingers, said first hand being of a first size;

c) a second hand positioned proximally of the elongated body and having a form fitting glove with five control fingers for actuating the movable fingers of the first hand, wherein each control finger is configured to receive a corresponding finger of a user's hand said second hand being of a second size which is greater than the first size of said first hand; and d) a plurality of control cables operatively connecting the movable fingers of the first hand and the control fingers of the second hand, whereby movement of one of the control fingers in a first direction causes the control cables to effect corresponding movement of the respective movable finger in the first direction.

26. An apparatus as recited in claim 25, further comprising a reduction assembly operatively associated with the control cables for reducing input signals imparted to the control cables by the control fingers of the first hand.

27. An apparatus as recited in claim 26, wherein the first hand is approximately one fourth of the size of the second hand.

* * * * *